United States Patent [19]

Upadek et al.

[11] 4,372,880

[45] Feb. 8, 1983

[54] USE OF SUBSTITUTED 2-(1-METHYLBUTYL)-1,3-DIOXANES AS PERFUMING AGENTS

[75] Inventors: Horst Upadek, Erkrath; Klaus Bruns, Krefeld-Traar, both of Fed. Rep. of Germany

[73] Assignee: Henkel Kommanditgesellschaft auf Aktien, Düsseldorf-Holthausen, Fed. Rep. of Germany

[21] Appl. No.: 254,516

[22] Filed: Apr. 15, 1981

[30] Foreign Application Priority Data

Apr. 25, 1980 [DE] Fed. Rep. of Germany ....... 3016007

[51] Int. Cl.$^3$ .............................................. A61K 7/46
[52] U.S. Cl. ............................... 252/522 R; 549/369; 252/174.11
[58] Field of Search ..................... 252/522 R; 549/369

[56] References Cited

U.S. PATENT DOCUMENTS 3,423,430  1/1969  Cohn et al. ..................... 252/522 R
3,884,841  9/1975  Maessen et al. ................ 252/522 R
4,220,593  9/1980  Bruns et al. .................... 252/522 R

FOREIGN PATENT DOCUMENTS 7305488 10/1974 Netherlands ................... 252/522 R

*Primary Examiner*—John F. Niebling
*Attorney, Agent, or Firm*—Hammond & Littell, Weissenberger and Muserlian

[57] ABSTRACT

The invention is directed to a perfumery composition consisting essentially of at least one substituted 2-(1-methylbutyl)-1,3-dioxane and customary constituents and to the use of such a perfumery composition to impart a pleasant odor to a product.

20 Claims, No Drawings

USE OF SUBSTITUTED 2-(1-METHYLBUTYL)-1,3-DIOXANES AS PERFUMING AGENTS

FIELD OF THE INVENTION

This invention is directed to novel perfuming agents. More particularly, this invention is directed to the use of substituted 2-(1-methylbutyl)-1,3-dioxanes as perfuming agents as well as perfuming compositions containing such compounds.

OBJECTS OF THE INVENTION

It is an object of the invention to provide for the use of substituted 2-(1-methylbutyl)-1,3-dioxanes as perfuming agents.

It is also an object of the invention to provide perfuming compositions based upon substituted 2-(1-methylbutyl)-1,3-dioxanes.

These and other objects of the invention will become more apparent in the discussion below.

It has been found that substituted 2-(1-methylbutyl)-1,3-dioxanes of the general formula

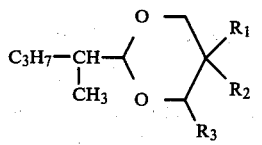

wherein $R_1$ is a hydrogen atom or a methyl or ethyl group; $R_2$ is a methyl, ethyl, n-propyl, isopropyl, n-butyl, or sec.-butyl group; and $R_3$ is a hydrogen atom or an n-propyl or isopropyl group, with the proviso that the sum of the carbon atoms of the radicals $R_1$, $R_2$, and $R_3$ is equal to or less than 6, can be used in an advantageous manner as perfumes or perfuming agents with a fruity or flowery aroma. At least one compound of Formula I is used as a perfuming agent in a perfume composition.

The substituted 2-(1-methylbutyl)-1,3-dioxanes to be used as perfuming agents according to the invention are prepared according to known methods of organic syntheses by acetalizing 2-methylpentanal with corresponding aliphatic 1,3-diols. The reaction proceeds according to the following reaction scheme:

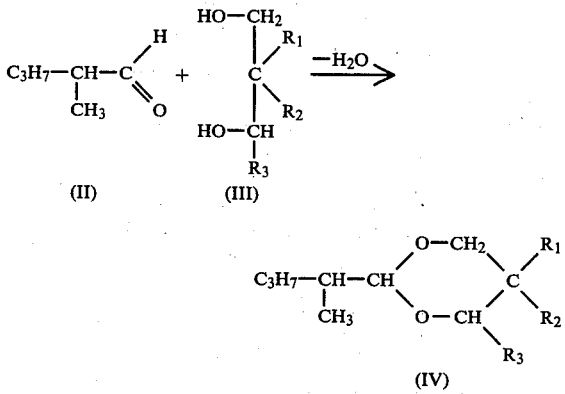

wherein the radicals $R_1$, $R_2$, and $R_3$ are as defined above.

Substituted 2-(1-methylbutyl)-1,3-dioxanes are themselves already known from the literature, such as, for example, P. Mastagli and C. de Fournas, Compt. Rend 250, (1960), p. 3336 to 3338, and T. Yvernault and M. Mazet, Bull. Soc. Chim. Fr. 1969, p. 638. However, neither of these publications provides any information about fragrance characteristics or suggests that such substituted 2-(1-methylbutyl)-1,3-dioxanes can be used advantageously as perfuming agents.

Compounds of Formula I that can be used according to the invention include, for example, 2-(1-methylbutyl)-5-methyl-5-n-propyl-1,3-dioxane, 2-(1-methylbutyl)-5,5-dimethyl-1,3-dioxane, 2-(1-methylbutyl)-5,5-dimethyl-4-n-propyl-1,3-dioxane, 2-(1-methylbutyl)-5,5-dimethyl-4-isopropyl-1,3-dioxane, 2-(1-methylbutyl)-5-ethyl-4-n-propyl-1,3-dioxane, 2-(1-methylbutyl)-5,5-diethyl-1,3-dioxane, 2-(1-methylbutyl)-5-methyl-5-sec.-butyl-1,3-dioxane, 2-(1-methylbutyl)-5-methyl-5-ethyl-1,3-dioxane, and 2-(1-methylbutyl)-5-ethyl-5-n-butyl-1,3-dioxane.

The substituted 2-(1-methylbutyl)-1,3-dioxanes of Formula I represent valuable perfuming agents with characteristic fruity or flowery aromas. A particular advantage is that they can be easily combined into novel fragrances. The compound 2-(1-methylbutyl)-5-methyl-5-n-propyl-1,3-dioxane, which has an interesting ligustrum/catechu note, is of particular importance.

The substituted 2-(1-methylbutyl)-1,3-dioxane to be used according to the invention can be mixed with other perfumes in various quantity ratios to provide new perfume compositions. Generally, the content of the substituted 2-(1-methylbutyl)-1,3-dioxanes in the perfume compositions will range from about 1 to 50 percent by weight, based on the weight of the total composition. Such compositions can serve directly as perfume or also as perfuming agents in cosmetics, such as creams, lotions, toilet waters, aerosols, mouth-care products, toilet soaps, and the like. Also, they may be used to improve the odor of industrial and commercial products such as detergents and cleansing agents, disinfectants, softeners, textile treatment agents, and the like. To perfume the various products, the perfume compositions containing the substituted 2-(1-methylbutyl)-1,3-dioxanes to be used according to the invention are added to the products generally in concentrations of from about 0.01 to 5, preferably from about 0.05 to 2, percent by weight, based on the total weight of the products.

The following examples are intended to illustrate the invention in greater detail and are not to be construed as limiting the invention thereto.

EXAMPLES

Examples 1 to 9

Several substituted 2-(1-methylbutyl)-1,3-dioxanes to be used according to the invention were prepared using a general preparation method. According to this method, 0.1 mol of 2-methylpentanal, 0.1 mol of the respective 1,3-alkanediol, 0.1 mol of orthoformic acid triethylester, and 0.5 g of p-toluenesulfonic acid were stirred for 1 hour at room temperature. Then a mixture of ethyl formate and ethanol was distilled off slowly. The cooled residue was taken up in ether, washed with soda solution and liquor, dried over sodium sulfate, concentrated, and distilled in the vacuum.

Compounds prepared and their characteristics are set forth in the following table:

TABLE

| Example | Compound | Perfume Note | Boiling Point (°C.) | Pressure (mbar) | Refractive Index ($n_D^{20}$) |
|---|---|---|---|---|---|
| 1 | 2-(1-methylbutyl)-5-methyl-5-n-propyl-1,3-dioxane | ligustrum-chatechu | 72 | 0.02 | 1.4421 |
| 2 | 2-(1-methylbutyl)-5,5-dimethyl-1,3-dioxane | fruity, carob bean | 75 | 9 | 1.4337 |
| 3 | 2-(1-methylbutyl)-5,5-dimethyl-4-n-propyl-1,3-dioxane | fruity, blueberry | 73 | 1.5 | 1.4397 |
| 4 | 2-(1-methylbutyl)-5,5-dimethyl-4-isopropyl-1,3-dioxane | fruity | 77 | 0.02 | 1.4405 |
| 5 | 2-(1-methylbutyl)-5-ethyl-4-n-propyl-1,3-dioxane | fruity, metallic, humus | 82 | 0.2 | 1.4422 |
| 6 | 2-(1-methylbutyl)-5,5-diethyl-1,3-dioxane | fruity, vigorose, strawberry | 77 | 1 | 1.4469 |
| 7 | 2-(1-methylbutyl)-5-methyl-5-sec.butyl-1,3-dioxane | metallic, geranium | 90 | 0.13 | 1.4495 |
| 8 | 2-(1-methylbutyl)-5-methyl-5-ethyl-1,3-dioxane | citronellol, isononyl alcohol, bran | 103 | 17 | 1.4404 |
| 9 | 2-(1-methylbutyl)-5-ethyl-5-n-butyl-1,3-dioxane | costus | 102 | 2 | 1.4488 |

A typical perfume composition containing a substituted 2-(1-methylbutyl)-1,3-dioxane is set forth below in Example 10. The substituted 2-(1-methylbutyl)-1,3-dioxanes mentioned in the example could readily be replaced by a similar such compound with the scope of the invention.

Example 10

Rose Complex

| Component | Amount (parts by weight) |
|---|---|
| 2-(1-methylbutyl-5,5-diethyl-1,3-dioxane | 100 |
| 2-(1-methylbutyl)-5-methyl-5-sec.butyl-1,3-dioxane | 60 |
| Citronellol | 250 |
| Citronellyl acetate | 120 |
| Phenylethyl alcohol | 100 |
| Methylionone | 100 |
| Bergamot oil | 90 |
| Citronellyl formiate | 80 |
| Cinnamic alcohol | 80 |
| Lemon oil | 5 |
| Hydroxycitronellal | 5 |
| Phenylacetaldehyde dimethylacetal | 5 |
| Nonanol | 4 |
| Nonanal | 1 |
| | 1000 |

The preceding specific embodiments are illustrative of the practice of the invention. It is to be understood, however that other expedients known to those skilled in the are or disclosed herein, may be employed without departing from the spirit of the invention or the scope of the appended claims.

We claim:

1. A perfumery composition consisting essentially of from about 1 to 50 percent by weight of at least one substituted 2-(1-methylbutyl)-1,3-dioxane of the formula

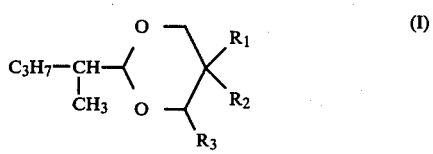

wherein $R_1$ is a hydrogen atom or a methyl or ethyl group; $R_2$ is a methyl, ethyl, n-propyl, isopropyl, n-butyl, or sec.-butyl group; and $R_3$ is a hydrogen atom or an n-propyl or isopropyl group, with the proviso that the sum of the carbon atoms of the radicals $R_1$, $R_2$, and $R_3$ is equal to or less than 6, as perfuming agent, and the remainder of customary constituents of perfumery compositions.

2. The composition of claim 1, wherein 2-(1-methylbutyl)-5-methyl-5-n-propyl-1,3-dioxane is present as perfuming agent.

3. The method of imparting a pleasant odor to a product comprising the step of adding to said product a sufficient amount of the perfumery composition of claim 1 to provide the desired degree of odor.

4. The method of claim 3, wherein the amount of perfumery composition added consists of from about 0.01 to 5 percent by weight, based on the weight of the total product.

5. The composition of claim 1, wherein 2-(1-methylbutyl)-5,5-dimethyl-1,3-dioxane is present as perfuming agent.

6. The method of imparting a pleasant odor to a product comprising the step of adding to said product a sufficient amount of the perfumery composition of claim 5 to provide the desired degree of odor.

7. The composition of claim 1, wherein 2-(1-methylbutyl)-5,5-dimethyl-4-n-propyl-1,3-dioxane is present as perfuming agent.

8. The method of imparting a pleasant odor to a product comprising the step of adding to said product a sufficient amount of the perfumery composition of claim 7 to provide the desired degree of odor.

9. The composition of claim 1, wherein 2-(1-methylbutyl)-5,5-dimethyl-4-isopropyl-1,3-dioxane is present as perfuming agent.

10. The method of imparting a pleasant odor to a product comprising the step of adding to said product a sufficient amount of the perfumery composition of claim 9 to provide the desired degree of odor.

11. The composition of claim 1, wherein 2-(1-methylbutyl)-5-ethyl-4-n-propyl-1,3-dioxane is present as perfuming agent.

12. The method of imparting a pleasant odor to a product comprising the step of adding to said product a sufficient amount of the perfumery composition of claim 11 to provide the desired degree of odor.

13. The composition of claim 1, wherein 2-(1-methylbutyl)-5,5-diethyl-1,3-dioxane is present as perfuming agent.

14. The method of imparting a pleasant odor to a product comprising the step of adding to said product a sufficient amount of the perfumery composition of claim 13 to provide the desired degree of odor.

15. The composition of claim 1, wherein 2-(1-methylbutyl)-5-methyl-5-sec.butyl-1,3-dioxane is present as perfuming agent.

16. The method of imparting a pleasant odor to a product comprising the step of adding to said product a sufficient amount of the perfumery composition of claim 15 to provide the desired degree of odor.

17. The composition of claim 1, wherein 2-(1-methylbutyl)-5-methyl-5-ethyl-1,3-dioxane is present as perfuming agent.

18. The method of imparting a pleasant odor to a product comprising the step of adding to said product a sufficient amount of the perfumery composition of claim 17 to provide the desired degree of odor.

19. The composition of claim 1, wherein 2-(1-methylbutyl)-5-ethyl-5-n-butyl-1,3-dioxane is present as perfuming agent.

20. The method of imparting a pleasant odor to a product comprising the step of adding to said product a sufficient amount of the perfumery composition of claim 19 to provide the desired degree of odor.

* * * * *